(12) United States Patent
Laurent et al.

(10) Patent No.: US 8,399,001 B2
(45) Date of Patent: Mar. 19, 2013

(54) COSMETIC COMPOSITION COMPRISING AT LEAST ONE GELLAN GUM OR DERIVATIVE THEREOF, AT LEAST ONE MONOVALENT SALT, AND AT LEAST ONE SUSPENSION COMPOUND, PROCESSES USING THIS COMPOSITION, AND USES THEREOF

(75) Inventors: Ludivine Laurent, Courbevoie (FR); Dorothée Pasquet, Bois-Colombes (FR)

(73) Assignee: L'Oreal, Paris (FR)

( * ) Notice: Subject to any disclaimer, the term of this patent is extended or adjusted under 35 U.S.C. 154(b) by 1122 days.

(21) Appl. No.: 10/990,476

(22) Filed: Nov. 18, 2004

(65) Prior Publication Data

US 2005/0169869 A1 Aug. 4, 2005

Related U.S. Application Data

(60) Provisional application No. 60/562,300, filed on Apr. 15, 2004.

(30) Foreign Application Priority Data

Nov. 18, 2003 (FR) ...................................... 03 13487

(51) Int. Cl.
*A61Q 5/06* (2006.01)
*A61Q 5/12* (2006.01)

(52) U.S. Cl. .......................... 424/401; 424/47; 424/70.11
(58) Field of Classification Search .......................... None
See application file for complete search history.

(56) References Cited

U.S. PATENT DOCUMENTS

| | | | |
|---|---|---|---|
| 2,047,398 A | 7/1936 | Voss et al. | |
| 2,723,248 A | 11/1955 | Wright | |
| 3,810,977 A | 5/1974 | Levine et al. | |
| 3,836,537 A | 9/1974 | Boerwinkle et al. | |
| 3,910,862 A | 10/1975 | Barabas et al. | |
| 3,925,542 A | 12/1975 | Viout et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 3,990,459 A | 11/1976 | Papantoniou | |
| 4,031,307 A | 6/1977 | DeMartino et al. | |
| 4,070,533 A | 1/1978 | Papantoniou et al. | |
| 4,076,912 A | 2/1978 | Papantoniou et al. | |
| 4,128,631 A | 12/1978 | Lundmark et al. | |
| 4,129,711 A | 12/1978 | Viout et al. | |
| 4,131,576 A | 12/1978 | Iovine et al. | |
| 4,137,208 A | 1/1979 | Elliott | |
| 4,165,367 A | 8/1979 | Chakrabarti | |
| 4,223,009 A | 9/1980 | Chakrabarti | |
| 4,282,203 A | 8/1981 | Jacquet et al. | |
| 4,289,752 A | 9/1981 | Mahieu et al. | |
| 4,693,935 A | 9/1987 | Mazurek | |
| 4,728,571 A | 3/1988 | Clemens et al. | |
| 4,957,732 A | 9/1990 | Grollier et al. | |
| 4,972,037 A | 11/1990 | Garbe et al. | |
| 5,190,927 A * | 3/1993 | Chang et al. | 514/54 |
| 5,425,939 A * | 6/1995 | Guerrero et al. | 424/78.02 |
| 5,523,078 A | 6/1996 | Baylin | |
| 5,538,717 A | 7/1996 | La Poterie | |
| 5,750,122 A * | 5/1998 | Evans et al. | 424/401 |
| 5,879,669 A * | 3/1999 | Clausen et al. | 424/70.11 |
| 6,051,250 A | 4/2000 | Ribier et al. | |
| 6,106,813 A | 8/2000 | Mondet et al. | |
| 6,110,473 A | 8/2000 | Fitzpatrick et al. | |
| 6,166,093 A | 12/2000 | Mougin et al. | |
| 6,180,122 B1 * | 1/2001 | Roulier et al. | 424/401 |
| 6,319,959 B1 | 11/2001 | Mougin et al. | |
| 6,372,876 B1 | 4/2002 | Kim et al. | |
| 6,391,288 B1 | 5/2002 | Miyazawa et al. | |
| 6,395,265 B1 | 5/2002 | Mougin et al. | |
| 6,399,050 B1 * | 6/2002 | Pasquet et al. | 424/70.12 |
| 6,624,125 B2 | 9/2003 | Trage et al. | |
| 6,770,271 B2 | 8/2004 | Mondet et al. | |
| 2002/0144356 A1 | 10/2002 | Kawai et al. | |
| 2002/0150546 A1 | 10/2002 | Mougin et al. | |
| 2002/0176836 A9 | 11/2002 | Belli et al. | |
| 2003/0033678 A1 | 2/2003 | Schulze zur Wiesche et al. | |
| 2003/0072779 A1 | 4/2003 | Sato et al. | |
| 2003/0072805 A1 | 4/2003 | Miyazawa et al. | |
| 2003/0143179 A1 | 7/2003 | Cao et al. | |
| 2003/0147833 A1 | 8/2003 | Rollat et al. | |
| 2003/0191271 A1 | 10/2003 | Mondet et al. | |
| 2005/0265949 A1 | 12/2005 | Rollat et al. | |

FOREIGN PATENT DOCUMENTS

| | | |
|---|---|---|
| DE | 2 330 956 | 1/1974 |
| EP | 0 080 976 | 6/1983 |
| EP | 0 186 507 | 7/1986 |
| EP | 0 342 834 | 11/1989 |
| EP | 0 412 704 | 2/1991 |
| EP | 0 412 707 | 2/1991 |
| EP | 0 582 152 | 2/1994 |
| EP | 0 611 207 | 8/1994 |

(Continued)

OTHER PUBLICATIONS

Lubrizol, Fixative G-100 hair fixative polymer technical data sheet (Jan. 9, 2003).*

(Continued)

*Primary Examiner* — Jyothsna Venkat

(74) *Attorney, Agent, or Firm* — O'Brien Jones, PLLC

(57) ABSTRACT

Disclosed herein is a liquid or fluid aqueous cosmetic composition comprising, in a cosmetically acceptable medium, at least one gellan gum or derivative thereof, at least one monovalent salt, and at least one suspension compound chosen from silicones and fatty substances. Further disclosed herein is a process for shaping and/or holding a hairstyle, in which the cosmetic composition is used, as well as the uses of this cosmetic composition as a styling composition for fixing and holding the hair, a haircare composition, a hair conditioning composition for giving the hair softness, and a hair makeup composition.

10 Claims, No Drawings

FOREIGN PATENT DOCUMENTS

| | | |
|---|---|---|
| EP | 0 619 111 | 10/1994 |
| EP | 0 637 600 | 2/1995 |
| EP | 0 648 485 | 4/1995 |
| EP | 0 656 021 | 6/1995 |
| EP | 0 751 162 | 1/1997 |
| EP | 0 985 410 | 3/2000 |
| FR | 1 222 944 | 4/1959 |
| FR | 1 400 366 | 5/1963 |
| FR | 1 564 110 | 3/1968 |
| FR | 1 580 545 | 9/1969 |
| FR | 2 077 143 | 10/1971 |
| FR | 2 198 719 | 4/1974 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 2 589 476 | 5/1987 |
| FR | 2 743 297 | 7/1997 |
| GB | 839805 | 6/1960 |
| GB | 922457 | 4/1963 |
| GB | 1021400 | 3/1966 |
| GB | 1408388 | 10/1975 |
| GB | 1572626 | 7/1980 |
| GB | 2384705 | 8/2003 |
| JP | 0-2144067 | 6/1990 |
| JP | 2-295912 | 6/1990 |
| JP | 9-020649 | 1/1997 |
| JP | 11-335691 | 12/1999 |
| LU | 75370 | 7/1976 |
| LU | 75371 | 7/1976 |
| WO | WO-93/23009 | 11/1993 |
| WO | WO-93/23446 | 11/1993 |
| WO | WO-94/03510 | 2/1994 |
| WO | WO-95/00578 | 1/1995 |
| WO | WO-01/28503 | 4/2001 |
| WO | WO 2005/072687 | 8/2005 |

OTHER PUBLICATIONS

English language Derwent Abstract of EP 0 080 976, Jun. 8, 1983.
English language Derwent Abstract of FR 2 357 241, Feb. 3, 1978.
English language Derwent Abstract of FR 2 589 476, May 7, 1987.
English language Derwent Abstract of JP 0-2144067, Jun. 1, 1990.
English language Derwent Abstract of JP 2-295912, Jun. 12, 1990.
English language Derwent Abstract of JP 9-020649, Jan. 21, 1997.
English language Patent Abstracts of Japan Abstract of JP 11-335691, Dec. 7, 1999.
French Search Report for FR 0 313 487, dated Jun. 3, 2004.
Duliba, et al. "Clarified High Acyl High Molecular Weight Gellan Gum Applications," Research Disclosure, Kenneth Mason Publications, vol. 463, No. 7, 2002.
Swazey, "Gellan Gum in Toothpaste,"Research Disclosure, Kenneth Mason Publications, vol. 440, No. 130, 2000.
Tang, et al. "Compression Strength and Deformation of Gellan Gels Formed with Mono- and Divalent Cations," Carbohydrate Polymers, vol. 29, No. 1, pp. 11-16 (1996).
Todd & Byers, Cosmetics and Toiletries, "Volatile Silicone Fluids for Cosmetics," vol. 91, pp. 27-32 (Jan. 1976).
Patent Abstracts of Japan, Publication No. 02 157214, Publication Date Jun. 18, 1990.
Patent Abstracts of Japan, Publication No. 2001-131016, Publication Date May 15, 2001.
Patent Abstracts of Japan, Publication No. 2001-322920, Publication Date Nov. 20, 2001.
Patent Abstracts of Japan, Publication No. 2002-265314, Publication Date Sep. 18, 2002.
Patent Abstracts of Japan, Publication No. 2003-081826, Publication Date Mar. 19, 2003.
Patent Abstracts of Japan, Publication No. 2005-132828, Publication Date May 26, 2005.

* cited by examiner

COSMETIC COMPOSITION COMPRISING AT LEAST ONE GELLAN GUM OR DERIVATIVE THEREOF, AT LEAST ONE MONOVALENT SALT, AND AT LEAST ONE SUSPENSION COMPOUND, PROCESSES USING THIS COMPOSITION, AND USES THEREOF

This application claims benefit of U.S. Provisional Application No. 60/562,300, filed Apr. 15, 2004.

Disclosed herein is an aqueous liquid or fluid cosmetic composition comprising, in a cosmetically acceptable medium, at least one gellan gum or derivative thereof, at least one monovalent salt, and at least one suspension compound chosen from silicones and non-silicone fatty substances. Further disclosed herein is a process for shaping or holding a hairstyle in which this cosmetic composition is used, and also the uses of this composition.

It is common practice in the cosmetics field to use aqueous compositions comprising drops of silicone or of non-silicone fatty substances in suspension.

One problem posed by these compositions may be their stability. The stability of suspensions of drops of silicone or of fatty substances may be linked to the viscosity of the support; the stability is generally ensured by means of a surfactant. The composition obtained in the presence of surfactant(s) is an oil/water or silicone/water emulsion. Following a rise in temperature or simply over time, one may observe a drop in the viscosity of the emulsions. This drop in viscosity, if it is large enough, may cause phase separation of the emulsion. In general, it is difficult to obtain an emulsion that is stable over time.

Besides surfactants, all kinds of gelling agents have been used to obtain stable compositions.

European Patent Application No. EP 611 207 describes a process for stabilizing vesicles formed from a lipid-phase membrane containing at least one ionic and/or nonionic amphiphilic lipid encapsulating an aqueous phase, in the form of a dispersion in an aqueous phase, by addition to the aqueous dispersion phase of at least one stabilizer, the stabilizer being chosen from glycerol alginates, propylene glycol alginates, gellan gum, and welan gum.

It has now been discovered, surprisingly, that the use of a combination of at least one gellan gum or derivative thereof and at least one monovalent salt may make it possible to stabilize compositions comprising a compound in suspension.

The combination of at least one gellan gum or derivative thereof and at least one monovalent salt allows placing silicones and/or fatty substances in suspension, even in a medium of very low viscosity (from about 1 to 10 poises, i.e., 0.1 to 1 Pa·s). The cosmetic composition obtained may be stable for several months, even when it is subjected to variations in temperature.

One embodiment disclosed herein is a liquid or fluid aqueous cosmetic composition comprising, in a cosmetically acceptable medium, at least one gellan gum or derivative thereof, at least one monovalent salt, and at least one compound in suspension chosen from phenyl silicones, non-phenyl silicones, and non-silicone fatty substances, with the proviso that when the compound in suspension is not a phenyl silicone, then the composition comprises at least one fixing polymer chosen from at least one of anionic, cationic, amphoteric, and nonionic fixing polymers.

In certain embodiments, the cosmetic composition may be a cosmetic hair composition, such as a cosmetic hairstyling composition.

The thixotropic nature of the compositions disclosed herein may allow restitution of the properties of these cosmetic compositions when they are applied using a spray or as an aerosol.

According to one embodiment, the composition disclosed herein comprises at least one fixing polymer, in which case it may be used in styling cosmetic compositions for shaping and/or holding the hair.

The addition of at least one fixing polymer to the composition disclosed herein may make it possible to obtain a good hairstyle fixing effect, which is generally not the case for combinations of fixing polymers with silicones or conventional suspension agents.

Additionally, the cosmetic styling composition disclosed herein may give the hair good cosmetic properties, for example in terms of feel (soft feel), disentangling, and sheen.

When the combination is used in cosmetic compositions for shaping and/or holding the hairstyle, the compositions obtained may allow good fixing and good holding of the hair, i.e., a styling effect that persists throughout the day, or even for several days, which may have good water resistance and which may be easy to remove by shampooing.

Another embodiment disclosed herein is a process for shaping or holding the hairstyle, in which the disclosed cosmetic composition is used.

Yet another embodiment concerns the uses of this cosmetic composition as a styling composition for fixing and/or holding the hair, a haircare composition, a hair conditioning composition, for example for giving the hair softness, or a hair makeup composition.

Thus, the present disclosure relates to the use of a cosmetic composition for giving the hair a fixing effect, for giving the hair hold, and/or for giving the hair cosmetic qualities.

The cosmetic composition disclosed herein may be in the form of a spray, a mousse, or a gel.

Other embodiments, characteristics, aspects, and advantages of the cosmetic compositions will emerge even more clearly on reading the description and the examples that follow.

Without wishing to be bound by any theory, the cosmetic compositions a disclosed herein may be in the form of gels, i.e., a three-dimensional network of molecules that holds a large amount of solvent in its mesh. The formation of such a network constitutes its gelation.

The cosmetic compositions disclosed herein may also be in the form of mousses.

As used herein, the term "styling cosmetic composition" means a composition for shaping and/or holding the hairstyle.

As used herein, the term "liquid or fluid composition" means that the viscosity of the composition ranges from the viscosity of water to 50 poises, such as ranging from the viscosity of water to 20 poises.

As used herein, the term "aqueous composition" means that the cosmetically acceptable medium used in the compositions disclosed herein is a predominantly aqueous medium optionally comprising at least one additional organic solvent.

The additional organic solvent used in the compositions disclosed herein may be chosen from at least one of $C_1$-$C_4$ lower alcohols, for instance ethanol, isopropanol, tert-butanol, n-butanol, and polyols (for instance propylene glycol, polyol ethers, and mixtures thereof). The alcohol used may, for example, be ethanol.

The aqueous composition disclosed herein comprises less than 10% by weight of oily compounds; the term "oily compounds," as used herein, means both liquid and solid oily compounds.

Gellan gum is a polysaccharide produced by aerobic fermentation of *Sphingomonas elodea*, more commonly known as *Pseudomonas elodea*. This linear polysaccharide comprises a sequence of the following monosaccharides: D-glucose, D-glucuronic acid, and L-rhamnose. In the native state, gellan gum is highly acylated.

The gellan gum that may be used in the compositions disclosed herein is an at least partially deacylated gellan gum. This at least partially deacylated gellan gum is obtained by a high-temperature alkaline treatment.

A KOH or NaOH solution may be used, for example.

The purified gellan gum sold under the trade name Kelcogel® by the company Kelco is suitable for preparing the compositions disclosed herein.

The gellan gum derivatives are all products obtained by performing standard chemical reactions such as, for example, esterifications or additions of an organic or mineral acid salt.

An example of a gellan gum derivative that may be used is welan gum. Welan gum is a gellan gum modified by fermentation using the *Alcaligenes* strain ATCC 31 555. Welan gum has a repeating pentasaccharide structure formed from a main chain comprising D-glucose, D-glucuronic acid, and L-rhamnose units on which is grafted a pendent L-rhamnose or L-mannose unit.

The welan gum sold under the trade name Kelco Crete® by the company Kelco is suitable for preparing the compositions disclosed herein.

The concentration of the at least one gellan gum or derivative thereof used in the compositions disclosed herein may range from 0.005% to 10%, such as from 0.01% to 5%, or from 0.02% to 3%, by weight relative to the total weight of the composition.

The at least one monovalent salt that may be used in the compositions disclosed herein are salts of monovalent cations, such as alkali metal salts, ammonium salts, organic amine salts, and mixtures thereof. The monovalent cations of the alkali metals are the following cations: $Li^+$, $Na^+$, $K^+$, $Rb^+$, $Cs^+$, and $Fr^+$. $Na^+$, for example, may be used in the compositions disclosed herein.

The counterion is a mineral or organic anion, such as $Cl^-$.

The salt used may be NaCl.

The concentration of the at least one monovalent salt used in the compositions disclosed herein may range from 0.01% to 10%, such as from 0.05% to 5%, by weight relative to the total weight of the composition.

In certain embodiments, the monovalent salt/gellan gum ratio ranges from 1% to 50%, such as from 2% to 30%.

The silicones that may be used in the compositions disclosed herein may be linear, cyclic, branched or unbranched, and volatile or non-volatile. They may be in the form of oils, resins, or gums, and may, for example, be polyorganosiloxanes that are insoluble in the cosmetically acceptable medium.

The polyorganosiloxanes are defined in greater detail in Walter Noll's "Chemistry and Technology of Silicones" (1968) Academic Press. They can be volatile or non-volatile.

When they are volatile, the silicones may be chosen from those having a boiling point ranging from 60° C. to 260° C., and they may be chosen from:
(i) cyclic silicones having from 3 to 7, such as from 4 to 5, silicon atoms. These are, for example, octamethylcyclotetrasiloxane sold, for example, under the name Volatile Silicone 7207 by Union Carbide or Silbione® 70045 V 2 by Rhodia Chimie; decamethylcyclopentasiloxane sold under the name Volatile Silicone 7158 by Union Carbide, and Silbione® 70045 V 5 by Rhodia; and mixtures thereof.

Mention may also be made of dimethylsiloxane/methylalkylsiloxane cyclocopolymers, such as Volatile Silicone FZ 3109 sold by the company Union Carbide, having the chemical structure:

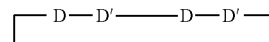

Mention may also be made of mixtures of cyclic silicones with organosilicon compounds, such as the mixture of octamethylcyclotetrasiloxane and tetratrimethylsilyl-pentaerythritol (50/50) and the mixture of octamethylcyclotetrasiloxane and oxy-1,1'-bis(2,2,2',2',3,3'-hexatrimethylsilyloxy)neopentane; and
(ii) linear volatile silicones having 2 to 9 silicon atoms and having a viscosity of less than or equal to $5\times10^{-6}$ $m^2/s$ at 25° C. An example is decamethyltetrasiloxane sold, for example, under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

Among the non-volatile silicones that may be mentioned are polyalkylsiloxanes, polyarylsiloxanes, polyalkylarylsiloxanes, silicone gums and resins, polyorganosiloxanes modified with organofunctional groups, and mixtures thereof.

The organomodified silicones that may be used in accordance with certain embodiments are silicones as defined above and containing in their structure at least one organofunctional group attached via a hydrocarbon-based group.

Among the organomodified silicones that may be mentioned are polyorganosiloxanes comprising:
polyethyleneoxy and/or polypropyleneoxy groups optionally comprising $C_6-C_{24}$ alkyl groups, such as the products known as dimethicone copolyol sold by the company Dow Corning under the name DC 1248, the oils Silwet® L 722, L 7500, L 77, and L 711 from the company Union Carbide, and the $(C_{12})$alkylmethicone copolyol sold by the company Dow Corning under the name Q2 5200;
substituted or unsubstituted amine groups, such as the products sold under the names GP 4 Silicone Fluid and GP 7100 by the company Genesee, and the products sold under the names Q2 8220 and Dow Corning 929 and 939 by the company Dow Corning. The substituted amine groups may be $C_1-C_4$ aminoalkyl groups;
thiol groups such as the products sold under the names GP 72 A and GP 71 from Genesee;
alkoxylated groups such as the product sold under the names Silicone Copolymer F-755 by SWS Silicones and Abil® Wax 2428, 2434 and 2440 by the company Goldschmidt;
hydroxylated groups such as the polyorganosiloxanes comprising a hydroxyalkyl function, described, for example, in French Patent Application No. FR A 85/16334;
acyloxyalkyl groups such as, for example, the polyorganosiloxanes described in U.S. Pat. No. 4,957,732;

carboxylic acid anionic groups, such as, for example, in the products described in European Patent No. EP 186 507 from the company Chisso Corporation, or alkylcarboxylic anionic groups, such as those present in the product X-22-3701E from the company Shin-Etsu; 2-hydroxyalkyl sulfonate; and 2-hydroxyalkyl thiosulfate, such as the products sold by the company Goldschmidt under the names Abil® S201 and Abil® S255;

hydroxyacylamino groups, such as the polyorganosiloxanes described in European Patent Application No. EP 342 834. Mention may be made, for example, of the product Q2-8413 from the company Dow Corning.

The silicone oils that may be used in the compositions disclosed herein are volatile or non-volatile polymethylsiloxanes comprising a linear or cyclic silicone chain, which are liquid or pasty at room temperature, for example cyclopolydimethylsiloxanes (cyclomethicones) such as cyclohexasiloxane; polydimethylsiloxanes comprising at least one of alkyl, alkoxy, and phenyl groups, which are pendent or at the end of a silicone chain, these groups having from 2 to 24 carbon atoms; phenylsilicones, for instance phenyltrimethicones, phenyidimethicones, phenyltrimethylsiloxydiphenylsiloxanes, diphenyldimethicones, diphenylmethyidiphenyltrisiloxanes, 2-phenylethyltrimethyl siloxysilicates, and polymethylphenylsiloxanes; and mixtures thereof.

The silicone gums that may be used in the compositions disclosed herein are polydiorganosiloxanes with a high molecular mass, ranging from 200,000 to 2,000,000, used alone or as a mixture in a solvent chosen from at least one of volatile silicones, polydimethylsiloxane oils, polyphenylmethylsiloxane oils, polydiphenyldimethylsiloxane oils, isoparaffins, methylene chloride, pentane, and hydrocarbons.

A silicone gum with a molecular weight of less than 1,500,000 may be used. The silicone gums may include, for example, polydimethylsiloxanes, polyphenylmethylsiloxanes, poly(diphenylsiloxanedimethylsiloxanes), poly(dimethylsiloxanemethylvinylsiloxanes), poly(dimethylsiloxanephenylmethylsiloxanes), and poly(diphenylsiloxanedimethylsiloxanemethylvinylsiloxanes).

These silicone gums may be terminated at a chain end with at least one of trimethylsilyl and dimethylhydroxysilyl groups.

The silicone resins that may be used in the compositions disclosed herein are crosslinked siloxane systems comprising at least one of the units $R_2SiO_{2/2}$, $RSiO_{3/2}$, and $SiO_{4/2}$, in which R is chosen from hydrocarbon-based groups having from 1 to 6 carbon atoms and phenyl groups. Among these products, mention may be made of those in which R is chosen from linear or branched lower ($C_1$-$C_6$) alkyl radicals and phenyl radicals.

The non-silicone fatty substances that may be used in the compositions disclosed herein may be chosen from natural or synthetic, organic or mineral non-silicone oils, waxes, and resins.

As used herein, an oil is a lipophilic compound that is liquid at room temperature (about 25° C.), with a reversible solid/liquid change of state. Animal oils and plant oils may comprise propane-1,2,3-triol triesters as constituents.

As oils that may be used according to certain embodiments, examples that may be mentioned include:
  hydrocarbon-based oils of animal origin, such as perhydrosqualene;
  hydrocarbon-based oils of plant origin, such as liquid triglycerides of fatty acids having from 4 to 10 carbon atoms, for instance heptanoic and octanoic acid triglycerides or alternatively, for example, sunflower oil, maize oil, soybean oil, marrow oil, grapeseed oil, sesame oil, hazelnut oil, apricot oil, macadamia oil, arara oil, castor oil, avocado oil, caprylic/capric acid triglycerides, for instance those sold by the company Stearineries Dubois or those sold under the names Miglyol 810, 812, and 818 by the company Dynamit Nobel, jojoba oil, and shea butter oil;
  synthetic esters and synthetic ethers, for example of fatty acids, such as oils of the formulae $R^6COOR^7$ and $R^6OR^7$ in which $R^6$ represents a fatty acid residue having from 8 to 29 carbon atoms and $R^7$ represents a branched or unbranched hydrocarbon-based chain having from 3 to 30 carbon atoms, such as, for example, purcellin oil, isononyl isononanoate, isopropyl myristate, 2-ethylhexyl palmitate, 2-octyldodecyl stearate, 2-octyldodecyl erucate, and isostearyl isostearate; hydroxylated esters such as isostearyl lactate, octyl hydroxystearate, octyldodecyl hydroxystearate, diisostearyl malate, triisocetyl citrate, fatty alkyl heptanoates, octanoates, and decanoates; polyol esters, for instance propylene glycol dioctanoate, neopentyl glycol diheptanoate, and diethylene glycol diisononanoate; and pentaerythritol esters, for instance pentaerythrityl tetraisostearate;
  linear or branched, mineral or synthetic hydrocarbons, such as volatile or non-volatile liquid paraffins and derivatives thereof, petroleum jelly, polydecenes, and hydrogenated polyisobutene such as parleam oil;
  fluid fatty alcohols having from 8 to 26 carbon atoms, for instance octyldodecanol, 2-butyloctanol, oleyl alcohol, linoleyl alcohol, and linolenyl alcohol;
  alkoxylated, such as ethoxylated fatty alcohols, for example oleth-12;
  partially hydrocarbon-based fluoro oils, for instance those described in the Japanese document JP A 2 295 912. Examples of fluoro oils which may also be mentioned include perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050 and PF 5060 by the company 3M; and bromoperfluorooctyl sold under the name Foralkyl® by the company Atochem; nonafluoromethoxybutane sold under the name MSX 4518 by the company 3M and nonafluoroethoxyisobutane; and perfluoromorpholine derivatives, such as the 4-trifluoromethylperfluoromorpholine sold under the name PF 5052 by the company 3M.

In the list of oils mentioned above, the term "hydrocarbon-based oil" means any oil predominantly comprising carbon and hydrogen atoms, and optionally comprising at least one of ester, ether, fluoro, carboxylic acid, and alcohol groups.

As used herein, a wax is a lipophilic compound that is solid at room temperature (about 25° C.), with a reversible solid/liquid change of state, having a melting point of greater than about 40° C. and which may be up to 200° C., and having an anisotropic crystal organization in the solid state. As constituents, the animal and plant waxes comprise carboxylic acid esters of long-chain alcohols. In general, the size of the wax crystals is such that crystals scatter and/or diffuse light, giving the composition comprising them a more or less opaque, cloudy appearance. By raising the wax to its melting point, it may be possible to make it miscible with oils and to form a microscopically homogeneous mixture, but on returning the temperature of the mixture to room temperature, a microscopically and macroscopically detectable recrystallization of the wax in the oils of the mixture may be obtained (opalescence).

As waxes that may be used according to certain embodiments, mention may be made of waxes of animal origin such as beeswax, spermaceti, lanolin wax, and lanolin derivatives; plant waxes such as sunflower wax, rice wax, apple wax, carnauba wax, candelilla wax, ouricury wax, Japan wax, cocoa butter, cork fiber wax, and sugarcane wax; mineral waxes, for example paraffin wax, petroleum jelly wax, lignite wax, microcrystalline waxes, ceresin, and ozokerite; synthetic waxes such as polyethylene waxes and Fischer-Tropsch waxes; and mixtures thereof.

The concentration of the at least one suspension compound chosen from silicones and non-silicone fatty substances used in the compositions disclosed herein may range from 0.01% to 20%, such as from 0.05% to 10%, by weight relative to the total weight of the composition.

Any anionic, cationic, amphoteric, or nonionic fixing polymers and mixtures thereof used in the art may be used in the styling compositions disclosed herein. Polymers that have only a thickening nature, such as the Carbopol® and Carbomer® products, are excluded.

The at least one fixing polymer may be soluble in the cosmetically acceptable medium or insoluble in this same medium and, in this case, used in the form of dispersions of solid or liquid polymer particles (lattices or pseudolattices).

The anionic fixing polymers generally used are polymers comprising groups derived from at least one of carboxylic acid, sulfonic acid, and phosphoric acid and have a number average molecular weight of ranging from 500 to 5,000,000.

The carboxylic groups are provided by unsaturated monocarboxylic or dicarboxylic acid monomers such as those corresponding to the formula (I):

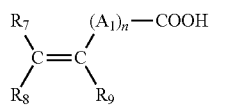

in which n is an integer ranging from 0 to 10; $A_1$ denotes a methylene group, optionally connected to the carbon atom of the unsaturated group or to the neighboring methylene group when n is greater than 1, via a hetero atom such as oxygen or sulfur; $R_7$ is chosen from hydrogen, phenyl groups, and benzyl groups; $R_8$ is chosen from hydrogen, lower alkyl groups, and carboxyl groups; and $R_9$ is chosen from hydrogen, lower alkyl groups, —$CH_2$—COOH, phenyl groups, and benzyl groups.

In the abovementioned formula, a lower alkyl group may denote a linear or branched group having 1 to 4 carbon atoms, such as methyl and ethyl.

The anionic fixing polymers comprising carboxylic groups that may be mentioned include:

A) acrylic or methacrylic acid homo- or copolymers, and salts thereof, such as the products sold under the names Versicol E or K by the company Allied Colloid and Ultrahold® by the company BASF, the acrylic acid copolymers and acrylamide copolymers sold as sodium salts under the names Reten 421, 423, and 425 by the company Hercules, and the sodium salts of polyhydroxycarboxylic acids.

B) copolymers of acrylic or methacrylic acid with a monoethylenic monomer such as ethylene, styrene, vinyl esters, acrylic acid esters, and methacrylic acid esters, optionally grafted onto a polyalkylene glycol such as polyethylene glycol and optionally crosslinked. Such polymers are described for example in French Patent No. 1 222 944 and German Patent Application No. 2 330 956, the copolymers of this type comprising an optionally N-alkylated and/or hydroxyalkylated acrylamide unit in their chain as described for example in Luxembourg Patent Application Nos. 75370 and 75371 or sold under the name Quadramer by the company American Cyanamid. Mention may also be made of copolymers of acrylic acid and of $C_1$-$C_4$ alkyl methacrylate and terpolymers of vinylpyrrolidone, of acrylic acid, and of methacrylate of $C_1$-$C_{20}$ alkyl, for example of lauryl, such as the product sold by the company ISP under the name Acrylidone® LM and methacrylic acid/ethyl acrylate/tert-butyl acrylate terpolymers such as the product sold under the name Luvimer® 100 P by the company BASF. Mention may also be made of methacrylic acid/acrylic acid/ethyl acrylate/methyl methacrylate copolymers as an aqueous dispersion sold under the name Amerhold® DR 25 by the company Amerchol.

C) crotonic acid copolymers, such as those comprising at least one of vinyl acetate and propionate units in their chain and optionally comprising other monomers such as allylic esters, and methallylic esters, vinyl ethers, and vinyl esters of a linear or branched saturated carboxylic acid with a long hydrocarbon chain such as those having at least 5 carbon atoms, it being possible for these polymers optionally to be grafted or crosslinked, or alternatively another vinyl, allylic, or methallylic ester monomer of an α- or β-cyclic. carboxylic acid. Such polymers are described, inter alia, in French Patent Nos. 1 222 944, 1 580 545, 2 265 782, 2 265 781, 1 564 110, and 2 439 798. Commercial products falling into this class are, for example, the resins 28-29-30, 26-13-14, and 28-13-10 sold by the company National Starch.

D) copolymers derived from $C_4$-$C_8$ monounsaturated carboxylic acids or anhydrides chosen from:
copolymers comprising (i) at least one of maleic, fumaric, and itaconic acids and anhydrides and (ii) at least one monomer chosen from vinyl esters, vinyl ethers, vinyl halides, phenylvinyl derivatives, and acrylic acid and its esters, the anhydride functions of these copolymers optionally being monoesterified or monoamidated. Such polymers are described for example in U.S. Pat. Nos. 2,047,398; 2,723,248; and 2,102,113 and British Patent No. GB 839 805, such as those sold under the names Gantrez® AN and ES by the company ISP,
copolymers comprising (i) at least one of maleic, citraconic, and itaconic anhydride units and (ii) at least one monomer chosen from allylic and methallylic esters optionally comprising at least one of acrylamide, methacrylamide, α-olefin, acrylic, and methacrylic esters, acrylic and methacrylic acids, and vinylpyrrolidone groups in their chain, the anhydride functions of these copolymers optionally being monoesterified or monoamidated.

These polymers are described, for example, in French Patent Nos. FR 2 350 384 and FR 2 357 241.

E) Polyacrylamides comprising carboxylate groups.

The homopolymers and copolymers comprising sulfonic groups are polymers comprising at least one of vinylsulfonic, styrenesulfonic, naphthalenesulfonic, and acrylamidoalkylsulfonic units.

These polymers may be chosen from:
polyvinylsulfonic acid salts having a molecular weight ranging from 1,000 to 100,000, as well as the copolymers with an unsaturated comonomer such as acrylic and methacrylic acids and their esters, as well as acrylamide and its derivatives, vinyl ethers, and vinylpyrrolidone;
polystyrenesulfonic acid salts such as the sodium salts that are sold under the names Flexan® 500 and Flexan® 130 by National Starch. These compounds are described, for example, in French Patent No. FR 2 198 719;

polyacrylamidesulfonic acid salts, such as those mentioned in U.S. Pat. No. 4,128,631 and polyacrylamido-ethylpropanesulfonic acid sold under the name Cosmedia® Polymer HSP 1180 by Henkel.

As another anionic fixing polymer, mention may be made of the branched block anionic polymer sold under the name Fixate® G100 by the company Noveon.

According to certain embodiments, the anionic fixing polymers may be chosen from acrylic acid copolymers, such as the acrylic acid/ethyl acrylate/N-tert-butylacrylamide terpolymers sold under the name Ultrahold® Strong by the company BASF; copolymers derived from crotonic acid, such as vinyl acetate/vinyl tert-butylbenzoate/crotonic acid terpolymers and the crotonic acid/vinyl acetate/vinyl neododecanoate terpolymers sold under the name Resin 28-29-30 by the company National Starch; polymers derived from at least one of maleic, fumaric, and itaconic acids, and anhydrides with vinyl esters, vinyl ethers, vinyl halides, phenylvinyl derivatives and acrylic acid and esters thereof, such as the methyl vinyl ether/monoesterified maleic anhydride copolymers sold under the name Gantrez® [lacuna] by the company ISP; the copolymers of methacrylic acid and of methyl methacrylate sold under the name Eudragit® L by the company Rohm Pharma; the copolymers of methacrylic acid and of ethyl acrylate sold under the name Luvimer® MAEX or MAE by the company BASF; the vinyl acetate/crotonic acid copolymers sold under the name Luviset® CA 66 by the company BASF; the vinyl acetate/crotonic acid copolymers grafted with polyethylene glycol sold under the name Aristoflex® A by the company BASF; and the polymer sold under the name Fixate® G100 by the company Noveon.

Among the anionic fixing polymers mentioned above, one may use the methyl vinyl ether/monoesterified maleic anhydride copolymers sold under the name Gantrez® ES 425 by the company ISP, the acrylic acid/ethyl acrylate/N-tert-butylacrylamide terpolymers sold under the name Ultrahold® Strong by the company BASF, the copolymers of methacrylic acid and of methyl methacrylate sold under the name Eudragit® L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymers of methacrylic acid and of ethyl acrylate sold under the name Luvimer® MAEX or MAE by the company BASF, the vinylpyrrolidone/acrylic acid/lauryl methacrylate terpolymers sold under the name Acrylidone® LM by the company ISP, and the polymer sold under the name Fixate® G100 by the company Noveon.

The cationic fixing film-forming polymers that may be used according to certain embodiments may be chosen from polymers comprising at least one of primary, secondary, tertiary, and quaternary amine groups forming part of the polymer chain or directly attached thereto, and having a number average molecular weight ranging from 500 to 5,000,000, such as from 1,000 to 3,000,000.

Among these polymers, mention may be made of the following cationic polymers:

(1) homopolymers or copolymers derived from at least one of acrylic esters, methacrylic esters, and amides with amine functions, and comprising at least one of the units of the following formulae:

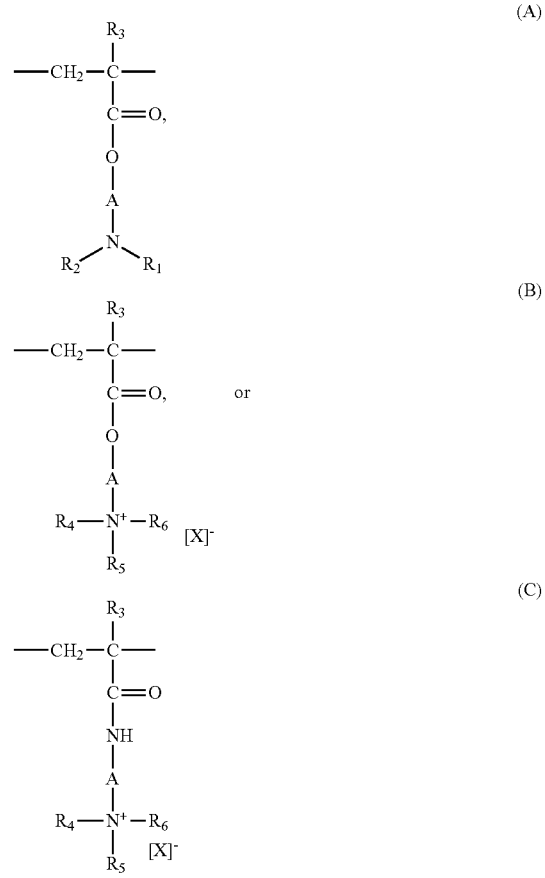

in which:

$R_3$ is chosen from hydrogen and $CH_3$ groups;

A is chosen from linear or branched alkyl groups comprising 1 to 6 carbon atoms and hydroxyalkyl groups comprising 1 to 4 carbon atoms;

$R_4$, $R_5$, and $R_6$, which may be identical or different, are chosen from linear or branched alkyl groups having from 1 to 18 carbon atoms and benzyl groups;

$R_1$ and $R_2$, which may be identical or different, are chosen from hydrogen and linear or branched alkyl groups having from 1 to 6 carbon atoms;

X is chosen from methosulfate anions and halides such as chloride and bromide.

The copolymers of the this group (1) may also comprise at least one comonomer unit that may be chosen from at least one of acrylamides, methacrylamides, diacetone acrylamides, acrylamides and methacrylamides substituted on the nitrogen with lower ($C_{1-4}$) alkyl groups, groups derived from acrylic and methacrylic acids and esters thereof, vinyllactams such as vinylpyrrolidone and vinylcaprolactam, and vinyl esters.

Thus, among these copolymers of the group (1), mention may be made of:

copolymers of acrylamide and of dimethylaminoethyl methacrylate quaternized with dimethyl sulfate or with a dimethyl halide, such as the one sold under the name Hercofloc® by the company Hercules, copolymers of acrylamide and of methacryloyloxyethyltrimethylammonium chloride, described, for example, in European Patent Application No. EP A 080 976 and sold under the name Bina Quat P 100 by the company Ciba Geigy, copolymers of acrylamide and of methacryloyloxyethyltrimethylammonium methosulfate, such as the product sold under the name Reten by the company Hercules, quaternized or non-quaternized vinylpyrrolidone/dialkylaminoalkyl acrylate and methacrylate copolymers, such as the products sold under the names Gafquat® by the company ISP, such as, for example, Gafquat® 734 and Gafquat® 755, and additionally the products known as Copolymer 845, 958 and 937. These polymers are described in detail, for example, in French Patent Nos. 2 077 143 and 2 393 573, fatty-chain polymers comprising a vinylpyrrolidone unit, such as the products sold under the names Styleze® W20 and Styleze® W10 by the company ISP, dimethylaminoethyl methacrylate/vinylcaprolactam/vinylpyrrolidone terpolymers, such as the product sold under the name Gaffix® VC 713 by the company ISP, and quaternized vinylpyrrolidone/dimethylaminopropylmethacrylamide copolymers, such as the products sold under the name Gafquat® HS 100 by the company ISP;

(2) cationic polysaccharides, such as those comprising quaternary ammonium, for example those described in U.S. Pat. Nos. 3,589,578 and 4,031,307, such as guar gums comprising at least one trialkylammonium cationic group. Such products are sold for example under the names Jaguar C13S, Jaguar C15, and Jaguar C17 by the company Meyhall;

(3) vinylpyrrolidone quaternary copolymers and vinylimidazole quaternary copolymers;

(4) chitosans and the salts thereof. The salts that may be used, for example, include chitosan acetate, lactate, glutamate, gluconate, and pyrrolidonecarboxylate.

Among these compounds, mention may be made of chitosan having a degree of deacetylation of 90.5% by weight, sold under the name Kytan Brut Standard by the company Aber Technologies, and chitosan pyrrolidonecarboxylate sold under the name Kytamer® PC by the company Amerchol.

(5) cationic cellulose derivatives such as copolymers of cellulose and of cellulose derivatives grafted with a water-soluble monomer comprising a quaternary ammonium, and disclosed for example in U.S. Pat. No. 4,131,576, such as hydroxyalkylcelluloses, for instance hydroxymethyl-, hydroxyethyl- and hydroxypropylcelluloses grafted for example with at least one of methacryloyloxyethyltrimethylammonium, methacrylamidopropyltrimethylammonium, and dimethyldiallylammonium salts.

The products sold corresponding to this definition may, for example, include the products sold under the names Celquat L 200 and Celquat H 100 by the company National Starch.

The amphoteric fixing polymers that can be used in accordance with certain embodiments may be chosen from polymers comprising units B and C distributed randomly in the polymer chain, in which B denotes a unit derived from a monomer comprising at least one basic nitrogen atom and C denotes a unit derived from an acid monomer comprising at least one of carboxylic and sulfonic groups, or alternatively B and C may denote groups derived from at least one of carboxybetaine and sulfobetaine zwitterionic monomers;

B and C may also denote a cationic polymer chain comprising at least one of primary, secondary, tertiary, and quaternary amine groups, in which at least one of the amine groups bears at least one of carboxylic and sulfonic groups connected via a hydrocarbon group, or alternatively B and C form part a polymer chain containing an α,β-dicarboxylic ethylene unit in which one of the carboxylic groups has been made to react with a polyamine comprising at least one of primary and secondary amine groups.

The amphoteric fixing polymers corresponding to the definition given above that may be mentioned may be chosen from the following polymers:

(1) copolymers having acidic vinyl and basic vinyl units, such as those resulting from the copolymerization of a monomer derived from a vinyl compound bearing a carboxylic group, such as acrylic acid, methacrylic acid, maleic acid, and α-chloroacrylic acid; and a basic monomer derived from a substituted vinyl compound containing at least one basic atom, such as dialkylaminoalkyl methacrylate, dialkylaminoalkyl acrylate, anddialkylaminoalkylmethacrylamides and -acrylamides. Such compounds are described, for example, in U.S. Pat. No. 3,836,537.

(2) polymers comprising units derived from:

a) at least one monomer chosen from acrylamides and methacrylamides substituted on the nitrogen atom with a linear or branched alkyl group, b) at least one acidic comonomer comprising at least one reactive carboxylic group, and c) at least one basic comonomer such as esters comprising at least one of primary, secondary, tertiary, and quaternary amine substituents of acrylic and methacrylic acids and the product of quaternization of dimethylaminoethyl methacrylate with at least one of dimethyl sulfate and diethyl sulfate.

The N-substituted acrylamides and methacrylamides that may be mentioned are compounds in which the alkyl groups have from 2 to 12 carbon atoms, such as N-ethylacrylamide, N-tert-butylacrylamide, N-tert-octylacrylamide, N-octylacrylamide, N-decylacrylamide, N-dodecylacrylamide, and the corresponding methacrylamides.

The acidic comonomers may be chosen from acrylic acid, methacrylic acid, crotonic acid, itaconic acid, maleic acid, fumaric acid, and alkyl monoesters, having 1 to 4 carbon atoms, of maleic and fumaric acids and anhydrides.

Basic comonomers that may be mentioned include aminoethyl, butyl-aminoethyl, N,N'-dimethylaminoethyl, and N-tert-butylaminoethyl methacrylates.

The copolymers whose CTFA (4th edition, 1991) name is octylacryl-amide/acrylates/butylaminoethyl methacrylate copolymer, such as the products sold under the names Amphomer® and Lovocryl® 47 by the company National Starch, may, for example, be used.

(3) crosslinked and acylated polyamino amides partially or totally derived from polyamino amides of general formula:

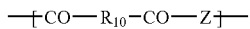

in which $R_{10}$ is chosen from divalent groups derived from a saturated dicarboxylic acid, a mono- or dicarboxylic aliphatic acid comprising an ethylenic double bond, esters of a lower alkanol of these acids having 1 to 6 carbon atoms; and groups derived from the addition of any one of said acids to a bis (primary) or bis(secondary) amine; and Z is chosen from groups derived from at least one of bis(primary), mono-, and bis(secondary) polyalkylene-polyamines, and may represent:

a) in an amount ranging from 60 to 100 mol %, the group:

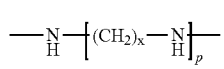
(II)

where x is 2 and p is chosen from 2 and 3, or alternatively x is 3 and p is 2, wherein this group is derived from at least one of diethylenetriamine, triethylenetetraamine, and dipropylenetriamine;

b) in an amount ranging from 0 to 40 mol %, the group

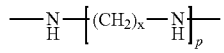
(II)

above in which x is 2 and p is 1 and which is derived from ethylenediamine, or the group derived from piperazine:

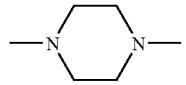

c) in proportions ranging from 0 to 20 mol %, the —NH(CH$_2$)$_6$-NH— group being derived from hexamethylenediamine, these polyamino amides being crosslinked by an addition reaction of a difunctional crosslinking agent chosen from epihalohydrins, diepoxides, dianhydrides, and bis-unsaturated derivatives, using from 0.025 to 0.35 mol of crosslinking agent per amine group of the polyamino amide and acylated by the action of at least one of acrylic acid, chloroacetic acid, alkane sultones, and salts thereof.

The saturated carboxylic acids may be chosen from acids having 6 to 10 carbon atoms, such as adipic acid, 2,2,4-trimethyladipic acid, and 2,4,4-trimethyladipic acid; terephthalic acid; and acids comprising an ethylenic double bond such as, for example, acrylic acid, methacrylic acid, and itaconic acid.

The alkane sultones used in the acylation may be chosen from propane sultone and butane sultone, and the salts of the acylating agents may be chosen from sodium and potassium salts.

(4) polymers comprising zwitterionic units of formula:

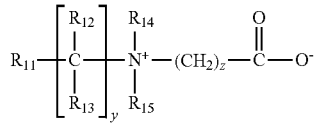
(IV)

in which $R_{11}$ is chosen from polymerizable unsaturated groups such as acrylate, methacrylate, acrylamide, and methacrylamide groups; y and z are chosen from an integer ranging from 1 to 3; $R_{12}$ and $R_{13}$ are chosen from hydrogen, methyl groups, ethyl groups, and propyl groups; and $R_{14}$ and $R_{15}$ are chosen from hydrogen and linear or branched alkyl groups such that the sum of the carbon atoms in $R_{14}$ and $R_{15}$ does not exceed 10.

The polymers comprising such units may also comprise units derived from nonzwitterionic monomers such as dimethylaminoethyl acrylate, diethylaminoethyl acrylate, methacrylate, alkyl acrylates, alkyl methacrylates, acrylamides, methacrylamides, and vinyl acetate.

By way of example, mention may be made of the copolymers of methyl methacrylate/methyl dimethylcarboxymethylammonioethyl methacrylate such as the product sold under the name Diaformer® Z301 by the company Sandoz.

(5) polymers derived from chitosan comprising monomer units corresponding to the following formulae:

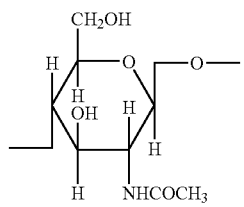
(D)

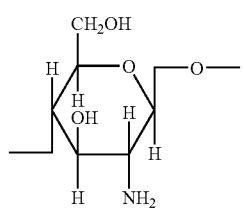
(E)

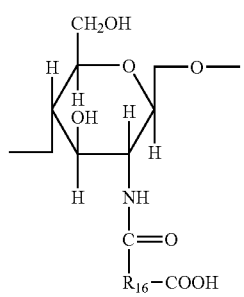
(F)

the unit (D) being present in an amount ranging from 0 to 30%, the unit (E) being present in an amount ranging from 5 to 50%, and the unit (F) being present in an amount ranging from 30% to 90%, it being understood that, in this unit (F), $R_{16}$ represents a group of formula:

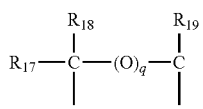

and the acid and base salts thereof, in which, if q is 0, $R_{17}$, $R_{18}$, and $R_{19}$, which may be identical or different, are independently chosen from hydrogen; methyl groups; hydroxyl groups; acetoxy groups; amino groups; monoalkylamine residues; dialkylamine residues that are optionally interrupted by at least one nitrogen atom and optionally substituted with at least one group chosen from amine, hydroxyl, carboxyl, alkylthio and sulfonic groups; and alkylthio residues in which the alkyl group bears an amino residue, at least one of the groups $R_{17}$, $R_{18}$, and $R_{19}$ being, in this case, a hydrogen atom;

or, if q is 1, $R_{17}$, $R_{18}$ and $R_{19}$ each represent hydrogen, (6) polymers corresponding to the general formula (V) that are described, for example, in French Patent No. 1 400 366:

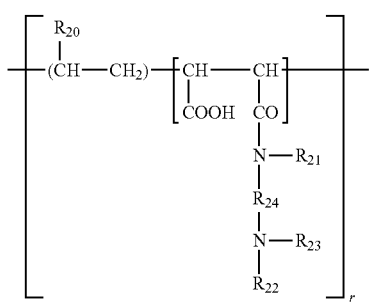

(V)

in which r is such that the molecular weight of the polymer ranges 500 to 6,000,000, such as from 1,000 to 1,000,000;

$R_{20}$ is chosen from hydrogen, $CH_3O$ groups, $CH_3CH_2O$ groups, and phenyl groups;

$R_{21}$ is chosen from hydrogen and lower alkyl groups such as methyl and ethyl groups; $R_{22}$ is chosen from hydrogen and $C_{1-6}$ lower alkyl groups such as methyl and ethyl groups;

$R_{23}$ is chosen from $C_{1-6}$ lower alkyl groups such as methyl and ethyl groups and groups corresponding to the formula: —$R_{24}$—$N(R_{22})_2$, wherein $R_{22}$ is defined as above and $R_{24}$ is defined as below, and $R_{24}$ is chosen from —$CH_2$—$CH_2$—, —$CH_2$—$CH_2$—$CH_2$—, and —$CH_2$—$CH(CH_3)$— groups, (7) polymers derived from the N-carboxyalkylation of chitosan, such as N-carboxymethylchitosan and N-carboxybutylchitosan sold under the name Evalsan by the company Jan Dekker.

(8) amphoteric polymers of the type -D-X-D-X- chosen from:

a) polymers obtained by the action of chloroacetic acid or sodium chloroacetate on compounds comprising at least one unit of formula:

-D-X-D-X-D- (VI)

where D denotes a group

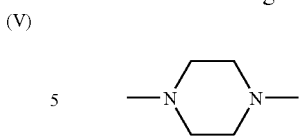

and X is chosen from the symbols E and E'. E and E', which may be identical or different, are chosen from divalent groups that are alkylene groups with a straight or branched chain having up to 7 carbon atoms in the main chain, which may be unsubstituted or substituted with hydroxyl groups and which optionally comprises, in addition to the oxygen, at least one of nitrogen, sulfur, and 1 to 3 aromatic and/or heterocyclic rings; the oxygen, nitrogen, and sulfur atoms being present in the form of at least one of ether, thioether, sulfoxide, sulfone, sulfonium, alkylamine, alkenylamine, hydroxyl, benzylamine, amine oxide, quaternary ammonium, amide, imide, alcohol, ester, and urethane groups.

b) polymers of formula:

-D-X-D-X- (VI')

where D denotes a group

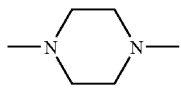

and X is chosen from the symbols E and E' and at least once E'; wherein E has the meaning given above and E' is a divalent group that is an alkylene group with a straight or branched chain having up to 7 carbon atoms in the main chain, which may be unsubstituted or substituted with at least one hydroxyl group and comprising at least one nitrogen atom, the nitrogen atom being substituted with an alkyl chain that is optionally interrupted by an oxygen atom and further comprising at least one of carboxyl functions and hydroxyl functions and betainized by reaction with at least one of chloroacetic acid and sodium chloroacetate.

(9) $(C_1-C_5)$alkyl vinyl ether/maleic anhydride copolymers partially modified by semiamidation with an N,N-dialkylaminoalkylamine such as N,N-dimethylaminopropylamine or by semiesterification with an N,N-dialkylaminoalkanol. These copolymers can also comprise other vinyl comonomers such as vinylcaprolactam.

Among the amphoteric fixing polymers described above, ones that may be mentioned according to certain embodiments are those of group (3), such as the copolymers whose CTFA name is octylacrylamide/acrylates/butylaminoethyl methacrylate copolymer, such as the products sold under the names Amphomer®, Amphomer® LV 71, and Lovocryl® 47 by the company National Starch and those of group (4) such as the copolymers of methyl methacrylate/methyl dimethylcarboxymethylammonioethyl methacrylate, sold, for example, under the name Diaformer® Z301 by the company Sandoz.

The nonionic fixing polymers that may be used according to certain embodiments may be chosen, for example, from:

polyalkyloxazolines;

vinyl acetate homopolymers;

vinyl acetate copolymers, for instance copolymers of vinyl acetate and of acrylic ester; copolymers of vinyl acetate and of ethylene; and copolymers of vinyl acetate and of maleic ester, for example of dibutyl maleate;

homopolymers and copolymers of acrylic esters, for instance copolymers of alkyl acrylates and of alkyl methacrylates, such as the products sold by the company Rohm & Haas under the names Primal® AC-261 K and Eudragit® NE 30 D, by the company BASF under the name 8845 and by the company Hoechst under the name Appretan N9212;

copolymers of acrylonitrile and of a nonionic monomer chosen, for example, from butadiene and alkyl (meth)acrylates; mention may be made of the products sold under the name CJ 0601 B by the company Rohm & Haas;

styrene homopolymers;

styrene copolymers, for instance copolymers of styrene and of an alkyl (meth)acrylate, such as the products Mowilith® LDM 6911, Mowilith® DM 611, and Mowilith® LDM 6070 sold by the company Hoechst, and the products Rhodopase SD 215 and Rhodopas® DS 910 sold by the company Rhône-Poulenc; copolymers of styrene, of alkyl methacrylate, and of alkyl acrylate; copolymers of styrene and of butadiene; and copolymers of styrene, of butadiene and of vinylpyridine;

polyamides;

vinyllactam homopolymers other than vinylpyrrolidone homopolymers, such as the polyvinylcaprolactam sold under the name Luviskol® Plus by the company BASF; and vinyllactam copolymers such as a poly(vinylpyrrolidone/vinyllactam) copolymer sold under the trade name Luvitec® VPC 55K65W by the company BASF, poly(vinylpyrrolidone/vinyl acetate) copolymers, such as those sold under the name PVPVA S630L by the company ISP, Luviskol® VA 73, VA 64, VA 55, VA 37, and VA 28 by the company BASF; and poly(vinylpyrrolidone/vinyl acetate/vinyl propionate) terpolymers, for instance the product sold under the name Luviskol® VAP 343 by the company BASF.

The alkyl groups of the nonionic polymers mentioned above may have from 1 to 6 carbon atoms.

According to present disclosure, it is also possible to use grafted silicone fixing polymers comprising a polysiloxane portion and a portion comprising a nonsilicone organic chain, one of the two portions constituting the main chain of the polymer, and the other being grafted onto the said main chain.

These polymers are described, for example, in Patent Application Nos. EP A 0 412 704, EP A 0 412 707, EP A 0 640 105, WO 95/00578, EP A 0 582 152, and WO 93/23009 and U.S. Pat. Nos. 4,693,935, 4,728,571, and 4,972,037.

These polymers may be amphoteric, anionic, or nonionic.

Such polymers are, for example, copolymers that can be obtained by free radical polymerization from the monomer mixture formed from:

a) 50 to 90% by weight of tert-butyl acrylate;
b) 0 to 40% by weight of acrylic acid;
c) 5 to 40% by weight of a silicone macromer of formula:

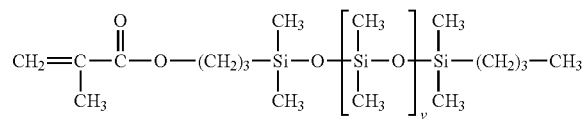

in which v is a number ranging from 5 to 700; the weight percentages being calculated relative to the total weight of the monomers.

Other examples of grafted silicone polymers include polydimethylsiloxanes (PDMSs) onto which are grafted, via a thiopropylene-type connecting chain, mixed polymer units of the poly(meth)acrylic acid type and of the polyalkyl (meth)acrylate type and polydimethylsiloxanes (PDMSS) onto which are grafted, via a thiopropylene-type connecting chain, polymer units of the polyisobutyl (meth)acrylate type.

Another type of silicone fixing polymer that may be mentioned is the product Luviflex® Silk, sold by the company BASF.

Functionalized or non-functionalized, silicone or non-silicone, and cationic, nonionic, anionic, or amphoteric polyurethanes may also be used as the at least one fixing polymer.

The polyurethanes that may be mentioned are those disclosed in European Patent Nos. EP 0 751 162, EP 0 637 600, EP 0 648 485, EP 0 656 021, and EP 0 619 111; French Patent No. FR 2 743 297; and PCT Patent Application No. WO 94/03510.

As polyurethanes that may be suitable according to certain embodiments, mention may be made of the products sold under the names Luviset® Pur and Luviset® Si-Pur by the company BASF.

The concentration of the at least one fixing polymer used in the compositions disclosed herein ranges from 0.1% to 20%, such as from 0.5% to 10%, by weight relative to the total weight of the composition.

The composition disclosed herein may also comprise at least one adjuvant chosen from nonionic, anionic, cationic, and amphoteric surfactants; nonionic, anionic, cationic and amphoteric additional polymers other than the fixing polymers used in the compositions disclosed herein; ceramides and pseudoceramides; vitamins and provitamins, including panthenol; silicone or non-silicone, liquid or solid, water-soluble and liposoluble sunscreens; solid compounds such as pigments, nacreous agents, and opacifiers; dyes; sequestering agents; plasticizers; solubilizers; acidifying agents; basifying agents; neutralizers; mineral and organic thickeners; antioxidants; hydroxy acids; glycols; penetrating agents; fragrances; and preserving agents.

A person skilled in the art will take care to select the optional additives and the amount thereof such that they do not harm the properties of the compositions disclosed herein.

These additives may be present in the composition in an amount ranging from 0 to 20% by weight relative to the total weight of the composition.

The examples that follow illustrate certain embodiments and should not be considered as limiting the present disclosure in any way.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The examples that follow are intended to illustrate the compositions disclosed herein without, however, limiting the scope.

EXAMPLES

Compositions formulated as a spray in a pump-dispenser bottle were prepared, in which the contents of the various constituents in g/100 g were as follows:

Composition 1

| Constituent | g/100 g |
|---|---|
| Gellan gum | 0.1 |
| NaCl | 0.5 |
| Phenyl silicone | 6 |
| Fragrance | qs |

-continued

| Constituent | g/100 g |
| --- | --- |
| Preserving agent | qs |
| Distilled water | qs 100 |

The phenyl silicone used was DC 556.

The drops remained in suspension in the medium, forming a stable homogeneous suspension. After storage for 2 months at 45° C., no change was observed in the appearance of this composition.

Composition 2

| Constituent | g/100 g |
| --- | --- |
| Gellan gum | 0.1 |
| NaCl | 0.5 |
| Phenyl silicone | 6 |
| Fixing polymer (Fixate-G-100) | 2 |
| Fragrance | qs |
| Preserving agent | qs |
| Distilled water | qs 100 |

The phenyl silicone used was DC 556.

When applied to the hair, this composition allowed a fixing effect compatible to a composition simply containing the fixing polymer at 2% in water.

Applying this composition to the hair gave the hair a styling effect and also a very soft feel and a good level of sheen.

What is claimed is:

1. A fluid aqueous cosmetic composition comprising, in a cosmetically acceptable medium:
   a partially deacylated gellan gum present in an amount ranging from 0.02% to 0.1%, by weight relative to the total weight of the composition;
   sodium chloride present in an amount ranging from 0.05% to 0.5%, by weight relative to the total weight of the composition;
   a phenyltrimethicone in suspension, present in an amount ranging from 0.05% to 6%, by weight relative to the total weight of composition, and
   an anionic fixing polymer chosen from AMP-acrylates/Allyl methacrylate copolymers present in an amount ranging from 0.5% to 2%, by weight relative to the total weight of the composition,
   wherein the fluid aqueous cosmetic composition is a styling cosmetic composition for the hair.

2. The composition according to claim 1, further comprising at least one adjuvant chosen from nonionic, anionic, cationic and amphoteric surfactants, nonionic, anionic, cationic and amphoteric additional polymers, ceramides and pseudoceramides, vitamins and provitamins, silicone or non-silicone, liquid or solid, water-soluble and liposoluble sunscreens, solid compounds, dyes, sequestering agents, plasticizers, solubilizers, acidifying agents, basifying agents, neutralizers, mineral and organic thickeners, antioxidants, hydroxy acids, glycols, penetrating agents, fragrances, and preserving agents.

3. The composition according to claim 2, wherein the provitamin is panthenol.

4. The composition according to claim 2, wherein the solid compounds are chosen from pigments, nacreous agents, and opacifiers.

5. The composition according to claim 1, wherein said composition is in the form of a gel.

6. The composition according to claim 1, wherein said composition is in the form of a mousse.

7. The composition according to claim 1, wherein said composition is in the form of a spray.

8. A process for shaping and/or holding a hairstyle, comprising applying to hair a fluid aqueous cosmetic composition according to claim 1.

9. A method for fixing and holding hair, comprising applying to the hair a fluid aqueous cosmetic composition according to claim 1.

10. A method for giving hair softness, comprising applying to the hair a fluid aqueous cosmetic composition according to claim 1.

* * * * *